United States Patent
Selmer-Olsen et al.

(10) Patent No.: US 6,753,031 B1
(45) Date of Patent: *Jun. 22, 2004

(54) AQUEOUS PRESERVATIVE

(75) Inventors: Ingvar Selmer-Olsen, Skårer (NO); Leif Hjørnevik, Skien (NO); Freddy Johnsen, Rånåsfoss (NO)

(73) Assignee: Norsk Hydro ASA, Oslo (NO)

( * ) Notice: Subject to any disclaimer, the term of this patent is extended or adjusted under 35 U.S.C. 154(b) by 0 days.

This patent is subject to a terminal disclaimer.

(21) Appl. No.: 09/762,821
(22) PCT Filed: Jul. 28, 1999
(86) PCT No.: PCT/NO99/00244
§ 371 (c)(1), (2), (4) Date: Apr. 23, 2001
(87) PCT Pub. No.: WO00/08929
PCT Pub. Date: Feb. 24, 2000

(30) Foreign Application Priority Data

Aug. 14, 1998 (NO) .......................................... 19983729

(51) Int. Cl.[7] ............................................. A23L 3/3454
(52) U.S. Cl. ..................... 426/532; 426/321; 426/331
(58) Field of Search ............................. 426/321, 331, 426/332, 643, 532

(56) References Cited

U.S. PATENT DOCUMENTS

| | | | |
|---|---|---|---|
| 4,220,661 A | * 9/1980 | Huitson | 424/317 |
| 4,724,149 A | * 2/1988 | Gul et al. | 426/310 |
| 4,978,546 A | * 12/1990 | Haram | 426/327 |
| 5,698,246 A | * 12/1997 | Villamar | 426/54 |
| 5,993,875 A | * 11/1999 | Hjornevik et al. | 426/327 |

FOREIGN PATENT DOCUMENTS

| | | | |
|---|---|---|---|
| EP | 0411827 | | 12/1993 |
| GB | 2012169 | * | 7/1979 |
| GB | 0411827 | * | 6/1991 |
| NO | wo 99/12435 | * | 3/1999 |
| WO | 93/16603 | | 9/1993 |
| WO | 9900023 | | 1/1999 |
| WO | 9912435 | | 3/1999 |

OTHER PUBLICATIONS

Abstract of Norwegian Patent No. 300,441 (Jun. 1997).
STN International, File CABA, CABA accession No. 86.42464, Document No. 860787067, Westgaard, P.: "Formic acid in a new form"; & Buskap og Avdratt, (1985) vol. 37, No. 4, pp. 246–247.
STN International, File CAPLUS, CAPLUS accession No. 1989:438263, Document No. 111:38263, Mitsui Toatsu Chemicals, Inc.: "Ammonium tetraformate–containing complete feed compositions and their manufacture"; & JP, A2, 01074955, Mar. 20, 1989.

* cited by examiner

*Primary Examiner*—Carolyn Paden
(74) *Attorney, Agent, or Firm*—Wenderoth, Lind & Ponack, L.L.P.

(57) ABSTRACT

The present invention relates to aqueous preservatives, containing ammonium tetraformate or any other combination of formic acid and ammonia, for grass and other agricultural crops, fish and fish products and meat products, having reduced corrosiveness and irritation to skin, comprising 0.5–5 weight % glycerol. Preferably the content of glycerol in the preservative is 0.75–1.5 weight %. The preservative may further contain at least one metal corrosion inhibitor and/or antioxidant.

8 Claims, 2 Drawing Sheets

AQUEOUS PRESERVATIVE

This application is a 371 application of PCT/NO 99/00244 filed Jul. 28, 1999.

BACKGROUND OF THE INVENTION

The present invention relates aqueous formic acid containing preservative for grass and other agricultural crops, fish and fish products and meat products, having reduced corrosiveness and irritation to skin.

Preserving high moisture grass as silage in anaerobic conditions has been common practice for many years. A fast drop in pH is important to inhibit plant respiration, enzymatic protein breakdown and development of undesired bacteria. The only desired process is the lactic acid fermentation, which stabilises the silage at low pH. The initial drop in pH from approximately 6 to about 4.5 is commonly obtained by adding formic acid at a rate of 2–5 litres/ton grass. Formic acid is the most widespread acid silage preservative mainly due to its efficient acidification and antimicrobial effect, according to J. M. Wilkinson et al. (1966) "Silage in Europe. A survey of 33 countries", Chalcombe Publications Ltd., Lincoln UK, and McDonald et al. (1991) "The Biochemistry of Silage", second Ed., Chalcombe Publications, Lincoln UK. Field surveys have shown that formic acid based silage additives have been the most efficient additive for high moisture grass (Nordang, L.Ø. "SurforundersØkelsen 1989–90", Faginfo, Statens fagtjeneste for landbruket, 6, 1991 and ADAS 1995, "Effect of additives on DM on fermentation", Grass Farmer, 57, 11). However, 85% formic acid has a high level of corrosion on skin and metal (machinery).

The principles of silage preservation of meat- and fish offals are basically the same as for grass. However, even more stress is put on an efficient acidifier to reduce the pH. This is because offal of animal origin contains very little sugar to produce lactic acid, and the buffering capacity is high.

Mixtures of formic acid and formate salts and also other organic acids (propionic acid and acetic acid and their respective salts) have been developed to reduce the corrosiveness of the acid product. The most successful formulation in terms of efficient preservation and success in major markets has been ammonium tetraformate, comprising about 64% formic acid, about 6% ammonia and the balance being water (EP-411.827B 1). The plain ammonia tetraformate (ATF) has been better than standard formic acid (85%) in terms of corrosion and burns to skin according to P. Westgaard, Journal Buskap og Avdraat, Vol. 37, pp 246–247, 1985. But it is still desired to reduce these negative properties of this efficient preservative. The corrosion on carbon steel has recently been overcome by addition of corrosion inhibitors such as cocobetaine or polyglycoside described in Norwegian Patent Application No. 974200. The skin corrosion is, however, still considered subject to improvements as ATF-type preservatives in this respect have to be labelled with "Corrosion" sign and the risk phrase "Causes burns".

The problem is to reduce the skin corrosion and at the same time maintain the same acidifying effect and good effect on silage fermentation quality. Just increasing the pH of the preservative might solve the problem of skin corrosion, however, it would produce new problems such as a less efficient preservative.

Known additives for reduction of metal corrosion have not been found to substantially reduce skin corrosion. Addition to preservatives of large amounts of lignosulphonates are claimed to reduce skin corrosion, but this will dilute the preservative and require use of relatively high amounts of preservative to obtain desired effect.

In the patent application WO 96/24247 there is stated that the aim is to obtain a preservative containing formic acid that has reduced corrosiveness on the skin, metal and machinery. A composition is made containing at least one ester of an unsubstituted or substituted benzoic acid with a $C_1$–$C_9$ alcohol or a mixture of such esters and another ester component of an unaromatic $C_1$–$C_{20}$ carboxylic acid with a $C_1$–$C_9$ alcohol. The preservative further contains at least one $C_1$–$C_4$ carboxylic acid. The preservative may contain 1.5–3 weight % of the ester mixture. This composition is stated to have excellent preservative effect. Data are however not given for corrosiveness with regard to metal or skin.

The main objective of the present invention was to arrive at an improved formic acid containing preservative being less corrosive and irritating to skin.

Another objective was to arrive at a preservative which could be classified as non-corrosive after a four hour skin exposure and thereby bring this type of preservatives from class "Corrosive to skin" (§3.2.5) to "Irritating to skin" (§3.2.6) as defined in Official Journal of the European Communities L 110A, Vol 36, May 4th, 1993 (Annex IV of Commission Directive 93/21EEC).

A further objective was to find a skin corrosion inhibitor which would be effective when applied in minor amounts and thereby avoid dilution or major change of the basic preservative.

In the search for a new solution to the skin corrosion problem related to preservatives it was first decided to concentrate on formic acid containing preservatives, primarily an ATF preservative. It was also essential to maintain the acidifying effect and good effect on silage fermentation quality. Accordingly, reduction of the acidity of the preservative was ruled out. Further checking on known metal anticorrosion agents revealed that their effect on the reduction on skin corrosion was only marginal. Both the corrosion inhibitor cocobetaine and the antioxidant ehtoxyquin were found to be insufficient with regard to reduction of skin corrosion. Thus the mode of action for inhibitors for metal corrosion seemed to be different from what was observed for skin corrosion. One inhibitor for steel corrosion which the inventors found useful to check further was glycerol which has been applied in some preservative in small amounts (0.5%). On skin. however, addition of glycerol to the ATF first seemed to have no effect, but when the amount added was substantially increased, it was surprisingly found that glycerol was able to bring ATF from class "Corrosive to skin" to class "irritating to skin". The main reason for investigating the effect of glycerol was that it is approved as feed additive in the EU list of additives (E422). Glycerol is further a valuable nutrient for animals and a substitute for several metabolic pathways.

A comprehensive lest program was then started to find the real effect of glycerol compared with other additives to preservatives. These tests proved that glycerol indeed gave a substantial reduction of skin corrosion of the preservative. The necessary amount for obtaining desired reduction in skin corrosion was found to depend on several factors such us the degree of neutralisation of the formic acid with ammonia. But already with addition of more than 0.5 weight % glycerol the skin corrosion started to go down. The upper limit for the glycerol content was found to be more a practical and economic limit in view of the fact that glycerol also is a nutrient. With regard to reduction of skin corrosion, however, it was found that for most cases 1.5 weight % would be sufficient.

SUMMARY OF THE INVENTION

Thus the preservative according to the invention contains ammonium tetraformate or any other combination of formic acid and ammonia and should contain 0.5–5 weight % glycerol.

Preferably the glycerol content in the preservative should be in the range 0.75–1.5 weight %.

The preservative may contain at least one metal corrosion inhibitor such as cocobetaine or alkyl glycoside. The preservative may also contain antioxidant.

BRIEF DESCRIPTION OF THE DRAWINGS

The invention is further explained and elucidated in connection with the description of the figures and the examples.

DETAILED DESCRIPTION OF THE INVENTION

EXAMPLE 1

Figure 1:
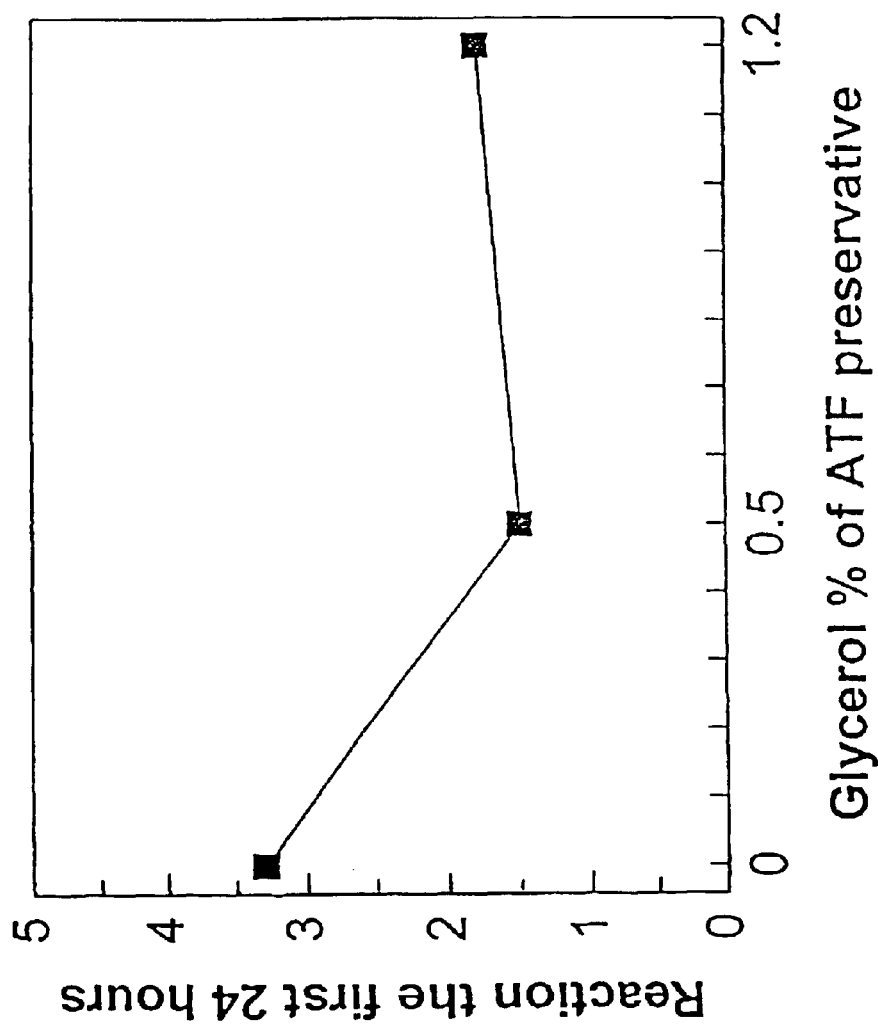
FIG. 1 shows the effect of glycerol in ATF on skin corrosion observed the first 24 hours after exposure.

This example shows the effect of ATF preservatives with various additives on test animals (Rabbits) exposed for four hours to the preservative. The tests were performed in compliance with that described in Annex to Commission Directive 92/69/EEC, Method B4 and OECD Guidelines for Testing of Chemicals, Method 404 (Official Journal of the European Communities L 383A, Vol.35, 29. Dec. 1992).

The animals were exposed to the samples on local areas of shaved skin for 4 hours. After that, skin reactions were recorded after 1 hour, 24 hours, 48 hours, 72 hours, 8 days, 15 days and 22 days. If there were severe burns to the skin with erosion and/or necrotic tissue, the animals were terminated very soon, and the degree of healing was not assessed. If the first animal showed severe signs of skin corrosion, further animals were not allowed to be exposed to the chemical. The animals who had milder reactions were kept until day 22. It is critical whether the test animals show a complete healing of the skin (regenerating skin with hair) or whether there are scars (permanent damage).

In order to present the skin reaction as a numerical parameter there were made a score for each observed effect. The mean value of the 3 (4) animals at an early stage (1–24 hours after exposure) was calculated for each sample. The degree of lasting skin damage was calculated from the readings at day 15–22 after exposure. If one animal out of three showed permanent damage (scar) at day 22 the product would be classified as corrosive. The lowest mean value (borderline) for a corrosive classification was therefore 1.7 (score 5 divided by 3 observations). The recorded results from the tests are shown in Table 1. In the two last columns the mean reaction scores are shown. Reactions and Reaction scores are defined below.

TABLE 1

| | | | | | | | | | | Reaction score | |
| --- | --- | --- | --- | --- | --- | --- | --- | --- | --- | --- | --- |
| | | | Time after completation of 4 hour exposure | | | | | | | Early | |
| Sample | pH | Animal | 1 h | 24 h | 48 h | 72 h | Day 8 | Day 15 | Day 22 | 1–24 h | Day 22 |
| ATF | 2.67 | 36 m | + | + | 0 | 0 | 0 | 0 | 0 | 3.3 | 3.3 |
| | | 45 m | +# | cb | cb | cb | pe | es,ns | ns@ | | |
| | | 46 m | +# | ce | ce | ce | pe | es,ns | ns@,sc | | |
| ATF + | 2.67 | 37 m | 0 | 0 | 0 | 0 | 0 | 0 | 0 | 3.5 | 1.8 |
| 0.2% | | 47 m | # | cb | cb | cb | cb,pe | sc3 | 0 | | |
| coco- | | 48 m | +# | ce | ce | ce | ce,pe | ns | 0 | | |
| betaine | | 61 f | ce | term. | term. | term. | term. | term. | term. | | |
| ATF + | 2.67 | 40 m | # | # | 0 | 0 | 0 | 0 | 0 | 3.5 | 1.8 |
| 2% | | 54 m | wh,# | cb | cb | cb | sc,cb,pe | sc2 | 0 | | |
| ethoxy-quin | | 55 m | wh,# | term. | term. | term. | term. | term. | term. | | |
| ATF + | 2.65 | 142 f | # | # | # | # | es1 | ns@ | term. | 1.5 | 3.6 |
| 0.5% | | 1522 f | wh,# | # | # | # | # | sc | ns@1 | | |
| glycerol | | 153 f | wh,# | # | # | # | # | sc | ns@1 | | |
| ATF + | 2.66 | 69 f | cb3 | cb3 | nc3 | nc3 | nc3 | nc3 | 0 | 1.8 | 0 |
| 1.2% | | 100 f | #,wh | #,wh | #,wh | #,wh | sc,# | ns | 0 | | |
| glycerol | | 101 f | 0 | 0 | 0 | 0 | 0 | 0 | 0 | | |

Definition of Reactions:

| | |
| --- | --- |
| 0 | no sign |
| wh | blanching |
| ns | new skin revealed |
| sc | scabbing |
| ph | petechial haemorrhage |
| at | atonia |
| term. | rabbit was killed due to cb/cs |
| cba | blanched area showing signs of chemical burn |
| cb | chemical burn (no erosion) |
| ce | corrosion/chemical burn-and areas of site eroded |

TABLE 1-continued

| | | | | | | | | | Reaction score | |
|---|---|---|---|---|---|---|---|---|---|---|
| | | | Time after completation of 4 hour exposure | | | | | | Early | |
| Sample | pH | Animal | 1 h | 24 h | 48 h | 72 h | Day 8 | Day 15 | Day 22 | 1–24 h | Day 22 | ns@    new skin with scar tissue (larger than 0.5 cm$^2$)
ns@1    new skin with scar tissue in small local foci.
pe    peeling
+    blue coloration to test site
fs    fissuring
brown coloration to test site
es    eschar
nc    necrotic tissue
Number after code indicates number of affected areas of the site.

Reaction Score (Mean)

A score is given for each observation based on the severity of the different reactions.

Early reactions (1–24 Hours After Exposure)

| Code | Reaction | Severity score |
|---|---|---|
| 0 | no sign | 0 |
| wh | blanching | 0.5 |
| + | Blue coloration to test site | 1.0 |
| # | brown coloration | 1.5 |
| ph | petechial haemorrhage | 1.5 |
| cba | blanched area showing signs of chemical burn | 3 |
| cb | chemical burn (no erosion) | 4 |
| ce | corrosion/chemical burn-and areas of site eroded | 5 |
| term. | rabbit was killed due to severe corrosion | 5 |

Healing reactions (day 22 After Exposure)

| Code | Healing reaction | Severity score |
|---|---|---|
| 0/ns | intact skin and hair/new skin | 0 |
| sc | scabbing | 2 |
| es1 | eschar, small local foci | 3 |
| ns@1 | new skin with scar tissue in small local foci | 3 |
| es | eschar large area | 5 |
| ns@ | new skin with scar tissue | 5 |
| term. | rabbit was killed due to lasting damage. | 5 |

From Table 1 and the FIG. 1 it can be seen that when at least 0.5 weight % of glycerol is added to the ATF preservative, the skin corrosion is substantially reduced. The addition of 0.5 weight % glycerol gave a significant reduction in the first skin reactions observed 1–24 hours after exposure. This amount of glycol was, however, too small to give a 100% protection of the dose site, and small local foci of scabbing and small local scars appeared on day 22.

Figure 2:
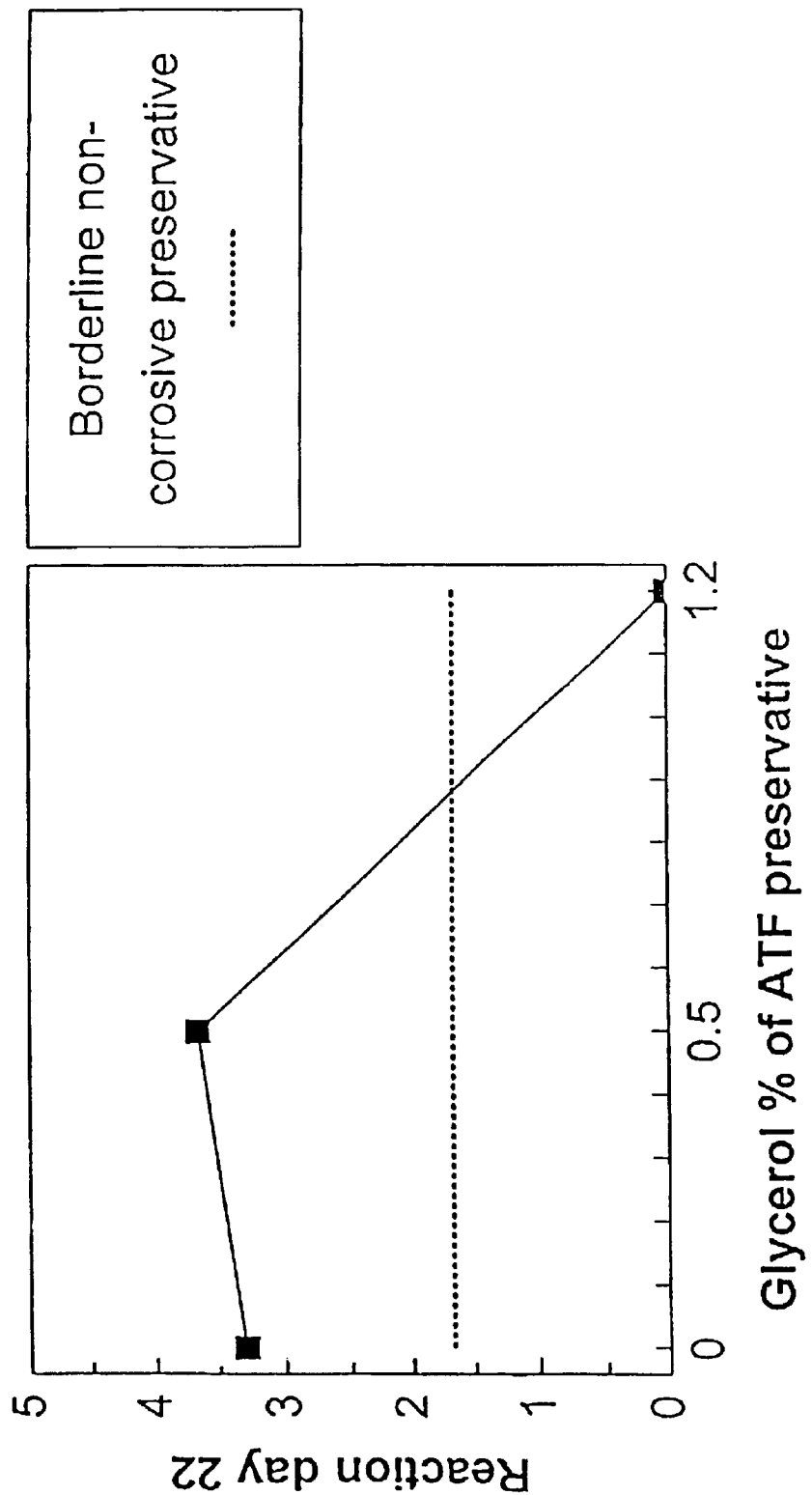
FIG. 2 shows the effect of glycerol in ATF on how the skin resolved 22 days after exposure. A borderline for the maximum skin effects allowed for a non-corrosive preservative is indicated by a dotted line.

From FIG. 2 it can be seen that a 1.2 weight % level of glycerol was enough to give full protection of the skin. Thus the new preservative can be classified as "Irritating to skin" contrary to the ATF without glycerol which is labelled "Corrosive to skin". It is further shown that when only 1.2 weight % glycerol is added, the severity score is well below that generally accepted (Borderline on FIG. 2).

What is claimed is:

1. An aqueous preservative, containing ammonium tetraformate or any other combination of formic acid and ammonia, having reduced corrosiveness and irritation to skin, containing 0.5–5 weight % glycerol.

2. The preservative according to claim 1, wherein the preservative contains 0.75–1.5 weight % glycerol.

3. A method of preserving grass, other agricultural crops, fish, fish products or meat products, which comprises applying thereto the aqueous preservative of claim 2.

4. The preservative according to claim 1, wherein the preservative contains at least one metal corrosion inhibitor and/or antioxidant.

5. A method of preserving grass, other agricultural crops, fish, fish products or meat products, which comprises applying thereto the aqueous preservative of claim 4.

6. The preservative according to claim 1, wherein the preservative contains cocobetaine or alkyl glycoside as metal corrosion inhibitor.

7. A method of preserving grass, other agricultural crops, fish, fish products or meat products, which comprises applying thereto the aqueous preservative of claim 6.

8. A method of preserving grass, other agricultural crops, fish, fish products or meat products, which comprises applying thereto the aqueous preservative of claim 1.

* * * * *